(12) United States Patent
Sun et al.

(10) Patent No.: US 10,881,354 B2
(45) Date of Patent: Jan. 5, 2021

(54) ONLINE REAL-TIME CORRECTION METHOD AND SYSTEM FOR POSITRON EMISSION TOMOGRAPHY DETECTOR

(71) Applicant: JIANGSU SINOGRAM MEDICAL TECHNOLOGY CO., LTD, Yangzhou (CN)

(72) Inventors: Dehui Sun, Yangzhou (CN); Heyu Wu, Yangzhou (CN)

(73) Assignee: JIANGSU SINOGRAM MEDICAL TECHNOLOGY CO., LTD, Yangzhou (CN)

( * ) Notice: Subject to any disclaimer, the term of this patent is extended or adjusted under 35 U.S.C. 154(b) by 189 days.

(21) Appl. No.: 15/747,943

(22) PCT Filed: Jun. 24, 2016

(86) PCT No.: PCT/CN2016/087079
§ 371 (c)(1),
(2) Date: Jan. 26, 2018

(87) PCT Pub. No.: WO2017/016353
PCT Pub. Date: Feb. 2, 2017

(65) Prior Publication Data
US 2018/0214085 A1    Aug. 2, 2018

(30) Foreign Application Priority Data
Jul. 27, 2015    (CN) .......................... 2015 1 0444962

(51) Int. Cl.
*A61B 6/00*    (2006.01)
*A61B 5/00*    (2006.01)
(Continued)

(52) U.S. Cl.
CPC ............ *A61B 5/7203* (2013.01); *A61B 6/037* (2013.01); *A61B 6/4258* (2013.01);
(Continued)

(58) Field of Classification Search
CPC ..... A61B 5/7203; A61B 6/037; A61B 6/4258; G01T 1/1647; G01T 1/40; G01T 1/2985; G01T 1/202; H04L 65/4076
See application file for complete search history.

(56) References Cited

U.S. PATENT DOCUMENTS 6,624,422 B2    9/2003    Williams et al.
7,579,599 B2    8/2009    Zhang et al.
(Continued)

FOREIGN PATENT DOCUMENTS

CN    101292174 A    10/2008
CN    104035122 A    9/2014
(Continued)

OTHER PUBLICATIONS

Knoess et al. Development of a daily quality check procedure for the High-Resolution Research Tomograph (HRRT) using natural LSO background radioactivity, IEEE Transactions on Nuclear Science vol. 49, No. 5, pp. 2074-2078 (Year: 2002).*
(Continued)

*Primary Examiner* — David P Porta
*Assistant Examiner* — Shun Lee
(74) *Attorney, Agent, or Firm* — Kolitch Romano LLP

(57) ABSTRACT

An online real-time correction method and system for a positron emission tomography (PET) detector. The method includes: acquiring a drifted channel number of a peak position of a full-energy peak in a drifted energy spectrum after a gain value of a PET detector system has changed and a ratio of a currently accumulated energy of each signal channel to a current total accumulated energy of all signal channels; substituting the above parameters, an initial channel number of the peak position of the full-energy peak in an initial energy spectrum and a ratio of an initially accumulated energy of each signal channel to a total initially
(Continued)

accumulated energy of all of the signal channels in the PET detector system into a gain adjustment ratio calculation formula to calculate a gain adjustment ratio; and adjusting, according to the gain adjustment ratio, a gain value of the PET detector system.

20 Claims, 8 Drawing Sheets

(51) Int. Cl.
| | | |
|---|---|---|
| G01T 1/202 | (2006.01) | |
| G01T 1/164 | (2006.01) | |
| G01T 1/40 | (2006.01) | |
| A61B 6/03 | (2006.01) | |
| G01T 1/29 | (2006.01) | |
| H04L 29/06 | (2006.01) | |

(52) U.S. Cl.
CPC ............ *G01T 1/1647* (2013.01); *G01T 1/202* (2013.01); *G01T 1/2985* (2013.01); *G01T 1/40* (2013.01); *H04L 65/4076* (2013.01)

(56) References Cited

U.S. PATENT DOCUMENTS

| | | | |
|---|---|---|---|
| 2004/0016884 A1* | 1/2004 | Williams | ............ G01T 1/2985 |
| | | | 250/363.09 |
| 2013/0009047 A1 | 1/2013 | Grazioso et al. | |
| 2013/0193330 A1* | 8/2013 | Wagadarikar | ......... G01T 1/1648 |
| | | | 250/362 |
| 2013/0214168 A1 | 8/2013 | McDaniel et al. | |

FOREIGN PATENT DOCUMENTS

| | | |
|---|---|---|
| CN | 105182399 A | 12/2015 |
| JP | 2010160045 A | 7/2010 |
| JP | 2011089901 A | 5/2011 |

OTHER PUBLICATIONS

International Search Report dated Sep. 30, 2016 of corresponding International application No. PCT/CN2016/087079; 2 pgs.

* cited by examiner

ONLINE REAL-TIME CORRECTION METHOD AND SYSTEM FOR POSITRON EMISSION TOMOGRAPHY DETECTOR

This application claims the priority of Chinese Patent Application No. 201510444962.0 filed on Jul. 27, 2015 to the Chinese Patent Office with a title of "Online Real-Time Correction Method for Positron Emission Tomography Detector", the entire disclosure of which is hereby incorporated in this application by reference.

TECHNICAL FIELD

The present disclosure relates to but is not limited to the following fields: nuclear medicine and high-energy physics, in particular to the real-time adjustment of the stability of a detector, and more particularly to an online real-time correction method and system for a positron emission tomography detector.

BACKGROUND

Since most detector systems for PET (Positron Emission Tomography) are limited by the scale and cost of a detector size readout system, it is difficult to read out signals generated by each channel of crystals independently, but the light generated by the crystals will be encoded by a lightguide, and a few detectors and a two-dimensional image decoding manner will be used to complete the task.

No matter whether a traditional modular structure is adopted, or detectors are shared and the like, the essence is the use of several fixed-position detectors, related detector signals are summated to obtain a total energy of light-emitting crystals, and the positions of the light-emitting crystals in a crystal array can be determined via a centroid method.

Based on this principle, the system needs to generate a corresponding position lookup table for each module while leaving from a factory, thereby determine the position of the hit crystal. The system needs to generate an energy lookup table to select cases of energy range of interest.

The effect of the system drift on PET in diagnosis is analyzed as follows.

After a detector leaves from a factory, a gain value of the detector, such as a photomultiplier tube (PMT), has changed due to the effects of temperature, voltage, aging and other factors. Studies have shown that for every 1° C. change at room temperature, a PMT gain value changes by an average of 1%.

An isotope tracer used for PET is FDG (fluorodeoxyglucose) with a detection energy of 511 kev. Since all detectors have some energy resolution, for example, the energy resolution of an LYSO crystal is 13%, a window for screening this 511 kev energy is typically around 425 kev to 600 kev.

An energy spectrum of a 511 kev Gamma photon event generated by FDG detected by a detector shown in FIG. 1 contains a 511 keV energy peak at a channel 600, and a Compton scattering plateau.

As can be seen from FIG. 1: if the gain value of the detector changes, the measured peak position changes. The original 511 kev peak position is located at the channel 600, and an energy window is set at channels 500 to 700 within a dotted line. That is to say, signals detected by the detector falling within the energy window are all considered 511 kev events. However, if the gain of the detector or amplifier changes dramatically, the energy peak moves towards a lower energy region (a dashed gray line in the figure), and the Compton scattering plateau will enter the energy window, resulting in a significant increase in scattering cases of the system. The energy peak moves to a high energy region, resulting in a 511 kev peak moving out of the energy window and an actual decrease in effective case rate.

In particular, when the gain value of the relevant detector for determining a signal position changes non-uniformly, an analyzed shape of the detector changes. If the system does not make relevant adjustments, the positioning of a crystal to which a single case belongs will change. When the system is drifted to a certain extent, the lookup table generated by the system and is used to determine the crystal, is no longer applicable, resulting in reduced detection efficiency of the system. The image uniformity changes.

If a PET detector fails to often re-calibrate the system, there is no guarantee that the PET detector will always be running at high performance.

An SUV (Standard Uptake Value) is a basic quantification parameter of PET diagnosis and plays an important role in the diagnosis and staging of cancer.

$$SUV = \frac{\text{Activity Concentration } (kBq/\text{ml})}{\text{Inj. dose}(MBq)/BodyWT \text{ (kg)}}$$

The SUV which reaches 2.5 typically will serve as a representative indication of a tumor. Statistical data show that: SUVmax has been proven to be an independent prognostic factor that is significantly associated with the survival time and the recurrence probability of a plurality of tumors and is also an important indicator of cancer staging. The accurate and stable SUV will help doctors make statistics and induction of patients, and also help doctors judge the diagnosis result and the treatment effect and make studies on postoperative recurrence and survival time.

Meanwhile, quantitative imaging is one of the important directions in medical research. Whether the PET detector operates stably is an important factor in determining the accuracy of the SUV. And these are also the aspects affected by the system drift mostly. That is to say, the drift of the system can have a very serious impact on the accurate measurement of the SUV.

Although there are still dose calculation, the patient's blood glucose metabolism level and other issues in terms of SUV quantification, the trouble caused by changes in the gain value of the PET detector system itself can be catastrophic.

Furthermore, the SUV will be used in clinical practice as an important reference for determining GTV (Gross Tumor Volume).

It can be seen, either from the diagnosis, or the scientific research perspective, that a stable PET is very important. When the drift of a peak position of an energy spectrum occurs due to change of the gain value of the PET detector system, the PET detector system must be corrected to adjust the gain value thereof to an initial state to ensure the accuracy of the output data of the PET detector system. Especially when the PET detector system includes a plurality of signal channels (i.e., including a plurality of photomultiplier tubes), the gain value for each signal channel should be individually corrected to further improve the accuracy of the PET detector system.

There are some correction methods in the industry at present.

1. In Siemens, the gain of a detector is adjusted by adjusting a dynode voltage. For example, in U.S. Pat. No.

7,579,599, in which the MD Anderson Gary Wong laboratory has done the corresponding study, it is not a good practice to adjust the dynode voltage to change the transit time. In an MD Anderson's design, an LED is used as a calibration source and cannot be applied during collection. The LED itself has voltage drift with temperature. In addition, there is a need for a feedback loop for voltage control, thereby virtually increasing the cost.

2. In GE's practice, such as U.S. Pat. No. 6,624,422, it is necessary to accumulate spectrums for each crystal of a detector, a higher processing capability is required, and therefore the cost of a circuit is increased. The processed spectral data needs to be synthesized to obtain a gain adjustment coefficient of each detector. However, it requires a large amount of data, a long adjustment period and a complicated circuit. Most importantly, the analyzed peak value is made up of four channels of related detector signals, and the signals affect each other and cannot accurately reflect the signal quality of a certain channel.

To sum up, in the process of implementing the present disclosure, the inventor finds that the prior art at least has the following problems: the existing correction method cannot adjust the gain value of each signal channel of the PET detector system respectively and requires a large amount of data and a long adjustment period.

SUMMARY

An objective of an embodiment of the present disclosure is to propose an online real-time correction method and system for a positron emission tomography (PET) detector, which can improve the accuracy of the output data of a PET detector.

Another objective of the embodiment of the disclosure is to provide an online real-time correction method and system for a positron emission tomography (PET) detector, which can adjust a gain of each signal channel in the PET detector system.

A yet another embodiment of the present disclosure is to provide an online real-time correction method and system for a positron emission tomography (PET) detector, which requires a small amount of data and a short adjustment period.

Specifically, the present disclosure comprises the following technical solution.

In the first aspect, an embodiment of the present disclosure provides an online real-time correction method for a positron emission tomography detector, comprising the following steps:

a. acquiring a drifted channel number of a peak position of a full-energy peak generated by self-decay of a scintillator containing a radioactive isotope, i.e., a current total peak position of a module, in a PET detector system in a drifted energy spectrum diagram after a gain value of the PET detector system has changed;

b. acquiring a ratio of a currently accumulated energy of each signal channel to a total currently accumulated energy of all signal channels in the PET detector system, i.e., a proportion of a current energy of each signal channel to a total energy, after the gain value of the PET detector system has changed;

c. substituting the current total peak position of the module, the proportion of the current energy of each signal channel to the total energy and a target total peak position of the module, and a proportion of a target energy of each signal channel to the total energy into the following formula to calculate a gain adjustment ratio of each signal channel:

$$A(x) = \frac{Pref * Gref(x)}{Pcur * Gcur(x)},$$

wherein, x represents a signal channel number which is an integer from 1 to N, and N is a total signal channel number in the PET detector system; A(x) is a gain adjustment ratio of a signal channel x; Pref is a target total peak position of the module; Gref(x) is a proportion of a target energy of the signal channel x to a total energy; Pcur is a current total peak position of the module; Gcur(x) is the current energy of the signal channel x to the total energy; the target total peak position of the module is an initial channel number of a peak position of a full-energy peak generated by self-decay of the scintillator containing the radioactive isotope in the PET detector system in an initial energy spectrum diagram; the proportion of the target energy of each signal channel to the total energy is a ratio of an initially accumulated energy of each signal channel to a total initially accumulated energy of all of the signal channels in the PET detector system; and d. performing gain adjustment to each signal channel respectively according to the gain adjustment ratio of each signal channel.

Further, the step a comprises: accumulating energies of all of the self-decay cases to form an energy spectrum after the gain value of the PET detector system has changed; and acquiring, according to the energy spectrum, a drifted channel number of a peak position of a full-energy peak generated by self-decay of a scintillator containing a radioactive isotope in the PET detector system in the drifted energy spectrum diagram after the gain value of the PET detector system has changed.

Further, the step a comprises: accumulating energies of all self-decay cases in a preset region to form an energy spectrum after the gain value of the PET detector system has changed; acquiring, according to the energy spectrum, a drifted channel number of peak positions of a plurality of full-energy peaks generated by self-decay of a scintillator containing a radioactive isotope in the PET detector system in the drifted energy spectrum diagram after the gain value of the PET detector system has changed; and calculating a sum or an average of the drifted channel numbers of the peak positions of the plurality of full-energy peaks to obtain the current total peak position of the module.

Further, the step b comprises: collecting a plurality of self-decay cases of the scintillator containing the radioactive isotope in the PET detector system after the gain value of the PET detector system has changed; calculating the currently accumulated energy of each signal channel in the plurality of self-decay cases of the scintillator containing the radioactive isotope; calculating the total currently accumulated energy of all the signal channels in the plurality of self-decay cases of the scintillator containing the radioactive isotope; and calculating the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

Further, the step b comprises: collecting the plurality of self-decay cases of the scintillator containing the radioactive isotope in the PET detector system after the gain value of the PET detector system has changed; calculating the currently accumulated energy of each signal channel which passes through a present energy window in the preset region in the plurality of self-decay cases of the scintillator containing the radioactive isotope; calculating the total currently accumulated energy of all of the signal channels which pass through the present energy window in the region in the plurality of self-decay cases of the scintillator containing the radioactive isotope; and calculating the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

Further, the correction method further comprises: acquiring the initial channel number of the peak position of the full-energy peak generated by self-decay of the scintillator containing the radioactive isotope in the PET detector system in the initial energy spectrum diagram of the PET detector system, i.e., the target total peak position of the module; and acquiring the ratio of the initially accumulated energy of each signal channel to the total initially accumulated energy of all of the signal channels in the PET detector system, i.e., a the proportion of the target energy of each signal channel to the total energy.

Further, the scintillator containing the radioactive isotope is a scintillator whose constituent atoms undergo self-decay.

Further, the scintillator containing the radioactive isotope is a scintillator containing $^{176}$Lu or a scintillator containing $^{138}$La.

Further, the scintillator containing $^{176}$Lu is selected from a scintillator containing $^{176}$Lu or a non-crystal containing $^{176}$Lu; the scintillator containing $^{138}$La is selected from a crystal containing $^{138}$La or a non-crystal containing $^{138}$La.

Further, the scintillation crystal containing $^{176}$Lu is selected from a LSO scintillation crystal or an LYSO scintillation crystal; the non-crystal containing $^{176}$Lu is selected from LuAG or LuAP; the crystal containing $^{138}$La is selected from a LaBr crystal.

Further, a correction method provided by an embodiment of the present disclosure comprises:

1) acquiring the initial channel number of the peak position of the full-energy peak generated by self-decay of the scintillator containing the radioactive isotope in an initial energy spectrum in the PET detector system, i.e., the target total peak position of the module; acquiring the ratio of the initially accumulated energy of each signal channel to the total accumulated energy of all of the initial signal channels in the PET detector, i.e., the proportion of the target energy of the signal channel x to the total energy;

2) acquiring the drifted channel number of the peak position of the full-energy peak generated by self-decay of the scintillator containing the radioactive isotope in the PET detector system in the drifted energy spectrum diagram, i.e., the current total peak position of the module; after acquiring, by the PET detector system, a plurality of self-decay cases of the scintillator collected randomly, calculating and outputting the accumulated energy of each signal channel in the plurality of self-decay cases of the scintillator; and calculating the current ratio of the accumulated energy of each signal channel to the total accumulated energy of all signal channels, i.e., the proportion of the current energy of the signal channel x to a total energy, in the plurality of self-decay cases of the scintillator;

3) calculating a gain adjustment ratio of each signal channel respectively according to the following formula:

$$A(x) = \frac{Pref * Gref(x)}{Pcur * Gcur(x)},$$

in which, x is an integer larger than or equal to 4; A(x) is the gain adjustment ratio of the signal channel x; Pref is the target total peak position of the module; Gref(x) is the proportion of a target energy of the signal channel x to the total energy; Pcur is the current total peak position of the module; Gcur(x) is the proportion of the current energy of the signal channel x to the total energy; and 4) performing, according to the gain adjustment ratio of each signal channel, gain adjustment for each signal channel.

Further, a correction method provided by an embodiment of the present disclosure comprises:

1) acquiring an initial channel number of a 307 kev initial peak position generated by $^{176}$Lu self-decay of an LYSO crystal in the PET detector system in the initial energy spectrum diagram, i.e., the target total peak position of the module; acquiring the ratio of the initially accumulated energy of each channel to the total accumulated energy of all of the initial signal channels in the PET detector, i.e., the proportion of the target energy of the signal channel x to the total energy;

2) acquiring a drifted channel number of a 307 kev initial peak position generated by $^{176}$Lu self-decay of the LYSO crystal in the PET detector system in the drifted energy spectrum diagram, i.e., the current total peak position of the module; after acquiring, by the PET detector system, a plurality of LYSO self-decay cases collected randomly, calculating and outputting the accumulated energy of each signal channel in the plurality of LYSO self-decay cases; and calculating the current ratio of the accumulated energy of each signal channel to the total accumulated energy of all signal channels, i.e., the proportion of the current energy of the signal channel x to the total energy, in the plurality of LYSO self-decay cases respectively;

3) calculating a gain adjustment ratio of each signal channel respectively according to the following formula:

$$A(x) = \frac{Pref * Gref(x)}{Pcur * Gcur(x)},$$

in which, x is an integer larger than or equal to 4; A(x) is the gain adjustment ratio of the signal channel x; Pref is the target total peak position of the module; Gref(x) is the proportion of the target energy of the signal channel x to the total energy; Pcur is the current total peak position of the module; Gcur(x) is the proportion of the current energy of the signal channel x to the total energy; and 4) performing gain adjustment for each signal channel according to the gain adjustment ratio of each signal channel.

In the second aspect, an embodiment of the present disclosure provides an online real-time correction system for a positron emission tomography detector, the correction system comprising a first acquisition module, a second acquisition module, a calculation module and an adjustment module, wherein the first acquisition module is configured to acquire a drifted channel number of a peak position of a full-energy peak generated by self-decay of a scintillator containing a radioactive isotope in the PET detector system in a drifted energy spectrum diagram, i.e., a current total peak position of a module, after a gain value of the PET detector system has changed; the second acquisition module is configured to acquire a ratio of a currently accumulated energy of each signal channel to a total currently accumulated energy of all signal channels in the PET detector system, i.e., a proportion of the current energy of each signal channel to a total energy, after the gain value of the PET detector system has changed; the calculation module is configured to substitute the current total peak position of the module, the proportion of the current energy of each signal channel to the total energy and a target total peak position of the module, and a proportion of a target energy of each signal channel to the total energy into the following formula to calculate a gain adjustment ratio of each signal channel:

$$A(x) = \frac{Pref * Gref(x)}{Pcur * Gcur(x)},$$

wherein, x represents a signal channel number which is an integer from 1 to N, and N is a total signal channel number in the PET detector system; $A(x)$ is a gain adjustment ratio of a signal channel x; Pref is a target total peak position of the module; $Gref(x)$ is a proportion of a target energy of the signal channel x to a total energy; Pcur is a current total peak position of the module; $Gcur(x)$ is a proportion of the current energy of the signal channel x to the total energy; the total target peak position of the module is an initial channel number of a peak position of a full-energy peak generated by self-decay of the scintillator containing the radioactive isotope in the PET detector system in an initial energy spectrum diagram; the proportion of the target energy of each signal to the total energy is a ratio of an initially accumulated energy of each signal channel to an initial total accumulated energy of all of the signal channels in the PET detector system; the adjustment module is configured to perform gain adjustment for each signal channel respectively according to the gain adjustment ratio of each signal channel.

Further, the first acquisition module is specifically configured to: accumulate energies of all the self-decay cases to form an energy spectrum after a gain value of the PET detector system has changed; acquire, according to the energy spectrum, a drifted channel number of a peak position of a full-energy peak generated by self-decay of a scintillator containing a radioactive isotope in the PET detector system in a drifted energy spectrum diagram after the gain value of the PET detector system has changed.

Further, the first acquisition module is specifically configured to: accumulate energies of all the self-decay cases in a preset region to form an energy spectrum after a gain value of the PET detector system has changed; acquire, according to the energy spectrum, a drifted channel number of peak positions of a plurality of full-energy peaks generated by self-decay of a scintillator containing a radioactive isotope in the PET detector system in a drifted energy spectrum diagram after the gain value of the PET detector system has changed; and calculate a sum or an average of the drifted channel number of the peak positions of the plurality of full-energy peaks to obtain the current total peak position of the module.

Further, the second acquisition module comprises: a collection unit configured to acquire a plurality of self-decay cases of the scintillator containing the radioactive isotope in the PET detector system after the gain value of the PET detector system has changed; a first calculation unit configured to calculate the currently accumulated energy of each signal channel in the plurality of self-decay cases of the scintillator containing the radioactive isotope; a second calculation unit configured to calculate the total currently accumulated energy of all of the signal channels in the plurality of self-decay cases of the scintillator containing the radioactive isotope; and a third calculation unit configured to calculate the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

Further, the collection unit is configured to acquire the plurality of self-decay cases of the scintillator containing the radioactive isotope in the PET detector system after the gain value of the PET detector system has changed; the first calculation unit is configured to calculate the currently accumulated energy of each signal channel which passes through a present energy window in the preset region in the plurality of self-decay cases of the scintillator containing the radioactive isotope; the second calculation unit is configured to calculate the total currently accumulated energy of all of the signal channels which pass through the present energy window in the region in the plurality of self-decay cases of the scintillator containing the radioactive isotope; the third calculation unit is configured to calculate the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

Further, the correction system further comprises: a third acquisition module configured to acquire the initial channel number of the peak position of the full-energy peak generated by self-decay of the scintillator containing the radioactive isotope in the PET detector system in the initial energy spectrum diagram of the PET detector system, i.e., the target total peak position of the module; a fourth acquisition module configured to acquire the ratio of the initially accumulated energy of each signal channel to the total initially accumulated energy of all of the signal channels in the PET detector system, i.e., the proportion of the target energy of each signal channel to the total energy.

Further, the scintillator containing the radioactive isotope is a scintillator whose constituent atoms undergo self-decay.

Further, the scintillator containing the radioactive isotope is a scintillator containing $^{176}$Lu or a scintillator containing $^{138}$La.

Further, the scintillator containing $^{176}$Lu is a scintillator containing $^{176}$Lu or a non-crystal containing $^{176}$Lu; the scintillator containing $^{138}$La is selected from a crystal containing $^{138}$La or a non-crystal containing $^{138}$La.

Further, the scintillation crystal containing $^{176}$Lu is a LSO scintillation crystal or an LYSO scintillation crystal; the non-crystal containing $^{176}$Lu is selected from LuAG or LuAP; the crystal containing $^{138}$La is selected from a LaBr crystal.

Further, in the correction system of the embodiment of the present disclosure, the third acquisition module is configured to acquire the initial channel number of the peak position of the full-energy peak generated by self-decay of the scintillator containing the radioactive isotope in the PET detector system in the initial energy spectrum diagram, i.e., the target total peak position of the module; the fourth acquisition module is configured to acquire the ratio of the initially accumulated energy of each signal channel to the total initially accumulated energy of all of the signal channels, i.e., the proportion of the target energy of the signal channel x to the total energy; the first acquisition module is configured to acquire the drifted channel number of the peak position of a full-energy peak generated by self-decay of the scintillator containing the radioactive isotope in the PET detector system in the drifted energy spectrum diagram, i.e., the current total peak position of the module; the second acquisition module is configured to: after acquiring, by the PET detector system, a plurality of self-decay cases of the scintillator collected randomly, calculate and output the accumulated energy of each signal channel in the plurality of self-decay cases of the scintillator; and calculate the current ratio of the accumulated energy of each signal channel to the total accumulated energy of all signal channels, i.e., the proportion of the current energy of the signal channel x to the total energy, in the plurality of self-decay cases of the scintillator containing the radioactive isotope; the calculation module is configured to calculate a gain adjustment ratio of each signal channel respectively according to the following formula:

$$A(x) = \frac{Pref * Gref(x)}{Pcur * Gcur(x)},$$

in which, x is an integer larger than or equal to 4; A(x) is the gain adjustment ratio of the signal channel x; Pref is the target total peak position of the module; Gref(x) is the proportion of the target energy of the signal channel x to the total energy; Pcur is the current total peak position of the module; Gcur(x) is the proportion of the current energy of the signal channel x to the total energy; the adjustment module is configured to, perform gain adjustment for each signal channel respectively according to the gain adjustment ratio of each signal channel.

Further, in the correction system provided by the embodiment of the present disclosure, the third acquisition module is configured to acquire an initial channel number of a 307 kev initial peak position generated by $^{176}$Lu self-decay of an LYSO crystal, in the PET system in an initial energy spectrum diagram, i.e., the target total peak position of the module; the fourth acquisition module is configured to acquire the ratio of the initially accumulated energy of each signal channel to the total accumulated energy of all of the initial signal channels, i.e., the proportion of the target energy of the signal channel x to the total energy in the PET detector; the first acquisition module is configured to acquire a drifted channel number of a 307 kev initial peak position generated by $^{176}$Lu self-decay of the LYSO crystal in the PET detector system in the drifted energy spectrum diagram, i.e., the current total peak position of the module; the second acquisition module is configured to: after acquiring, by the PET detector system, a plurality of LYSO self-decay cases collected randomly, calculate and output the accumulated energy of each signal channel in the plurality of LYSO self-decay cases; and calculate the current ratio of the accumulated energy of each signal channel to the total accumulated energy of all signal channels, i.e., the proportion of the current energy of the signal channel x to the total energy, in the plurality of LYSO self-decay cases respectively; the calculation module is configured to calculate the gain adjustment ratio of each signal channel respectively according to the following formula:

$$A(x) = \frac{Pref * Gref(x)}{Pcur * Gcur(x)},$$

in which, x is an integer larger than or equal to 4; A(x) is the gain adjustment ratio of the signal channel x; Pref is the target total peak position of the module; Gref(x) is the proportion of the target energy of the signal channel x to the total energy; Pcur is the current total peak position of the module; Gcur(x) is the proportion of the current energy of the signal channel x to the total energy; the adjustment module is configured to, perform gain adjustment for each signal channel respectively according to the gain adjustment ratio of each signal channel.

The technical solution provided by the embodiment of the present disclosure has the following beneficial effects.

In the correction method provided by the embodiment of the present disclosure, the PET detector system is corrected by using a self-decay effect of the scintillator containing the radioactive isotope in the PET detector system, and the gain value of the PET detector system is adjusted to an initial state. According to the correction method provided by the embodiment of the present disclosure, the gain value of each signal channel can be adjusted respectively. Meanwhile, few parameters are involved in the adjustment of the correction method provided by the embodiment of the present disclosure. For example, for a module that uses four channels of signals to analyze an array (i.e., containing four signal channels), and only five parameters needs to be determined to perform online real-time correction and adjustment. In addition, these five parameters are independent of each other and reflect the nature of the parameters corresponding to their own. Fewer parameters mean fewer data samples and faster adjustment speed. It can be found upon experiments that one adjustment can be achieved just by less than 10 seconds of data. It also means simpler implementation, lower probability of errors, and lower detection and maintenance costs. Using the self-decay effect of the scintillator containing the radioactive isotope widely used in the PET system, the PET detector system can be adjusted automatically without the need for a radioactive source, thereby eliminating the influences of radioactive source placement positions and other human factors, such that the correction result is more accurate.

BRIEF DESCRIPTION OF THE DRAWINGS

To describe the technical solution in the embodiments of the present disclosure more clearly, the accompanying drawings required for describing the embodiments are briefly introduced below. It is obvious that the accompanying drawings in the following description show merely some embodiments of the present disclosure, and those skilled in the art may still derive other drawings from these accompanying drawings without creative efforts.

DETAILED DESCRIPTION

Figure 1:
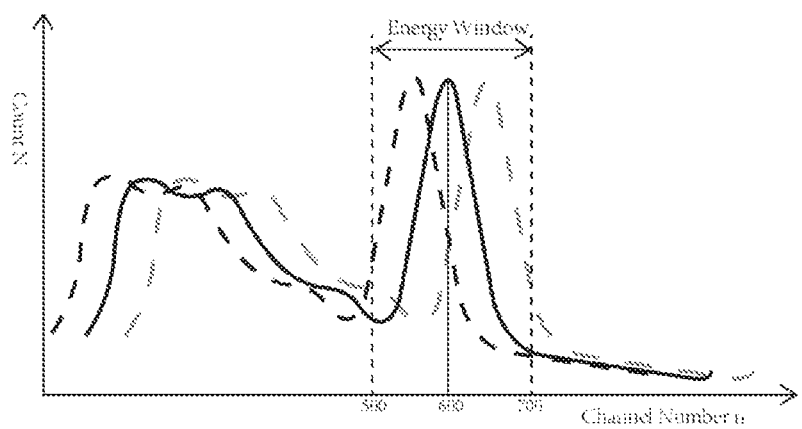
FIG. 1 is an energy spectrum diagram of a 511 kev Gamma photon event generated by FDG detected by a detector.

To make the objective, the technical solution and the advantages of the present disclosure clearer, the embodiments of the present disclosure are further described in detail below with reference to the accompanying drawings. Unless otherwise defined, all technical terms used in the embodiments of the present disclosure have the same meaning as commonly understood by those skilled in the art.

The present embodiment provides an online real-time correction method for a positron emission tomography (PET) detector, including the following steps.

In Step 101, a drifted channel number of a peak position of a full-energy peak generated by self-decay of a scintillator containing a radioactive isotope in a PET detector system, in a drifted energy spectrum after a gain value of the PET detector system has changed is acquired, i.e., a current total peak position of a module.

In Step 102, a ratio of a currently accumulated energy of each signal channel to a total current total accumulated energy of all signal channels in the PET detector system, i.e., a proportion of the current energy of each signal channel to a total energy, after the gain value of the PET detector system has changed is acquired.

In Step 103, the current total peak position of the module, the proportion of the current energy of each signal channel to the total energy and a target total peak position of the module, and a proportion of a target energy of each signal channel to the total energy are substituted into the following formula to calculate a gain adjustment ratio of each signal channel:

$$A(x) = \frac{Pref * Gref(x)}{Pcur * Gcur(x)},$$

wherein, x represents a signal channel number which is an integer from 1 to N, and N is a total signal channel number in the PET detector system; A(x) is a gain adjustment ratio of a signal channel x; Pref is a target total peak position of the module; Gref(x) is a proportion of a target energy of the signal channel x to a total energy; Pcur is a current total peak position of the module; Gcur(x) is a proportion of the current energy of the signal channel x to the total energy; the total target peak position of the module is an initial channel number of a peak position of a full-energy peak generated by self-decay of the scintillator containing the radioactive isotope in the PET detector system in an initial energy spectrum; the proportion of the target energy of each signal to the total energy is a ratio of an initially accumulated energy of each signal channel to a total initially accumulated energy of all of the signal channels in the PET detector system.

In Step 104, gain adjustment is performed for each signal channel respectively according to the gain adjustment ratio of each signal channel.

In the correction method provided by the present embodiment, the PET detector system is corrected by using a self-decay effect of the scintillator containing the radioactive isotope in the PET detector system. A gain adjustment ratio for each channel is calculated according to several parameters, such as the current total peak position of the module, the proportion of the current energy of each signal channel to the total energy, the target total peak position of the module and the proportion of the target energy of each signal channel to the total energy. The current gain value for each channel is adjusted a corresponding multiple according to the gain adjustment ratio, such that the gain value for each channel is restored to an initial state to realize correction of the PET detector system.

According to the correction method provided by the embodiment of the present disclosure, the gain value for each signal channel can be adjusted respectively. The adjustment of the correction method provided by the embodiment of the present disclosure relates to few parameters, and respective parameters are independent from each other and reflect the nature of the parameters corresponding to their own. Fewer parameters mean fewer data samples and faster adjustment speed. It can be found upon experiments that one adjustment can be achieved just by less than 10 seconds of data. It also means simpler implementation, lower probability of errors, and lower detection and maintenance costs. Using the self-decay effect of the scintillator containing the radioactive isotope widely used in the PET system, the PET detector system can be adjusted automatically without the need for a radioactive source, thereby eliminating the influences of radioactive source placement positions and other human factors, such that the correction result is more accurate.

The present embodiment provides an online real-time correction method for a positron emission tomography (PET) detector. When the initial gain value of the PET detector system changes due to the influences of voltage, temperature and other factors, resulting in the drift of the peak position of the energy spectrum, the gain value of the PET detector system is adjusted by the correction method provided by the present embodiment and thus restored to an initial state, thereby guaranteeing that the PET detector system works stably.

The correction method provided by the present embodiment is based on the Monte Carlo method. The gain adjustment ratio is calculated by using the characteristic that the scintillator containing the radioactive isotope used in the PET detector system will generate gamma photons during the self-decay process. The current gain value of the PET detector system is adjusted according to the gain adjustment ratio, such that the gain value of the PET detector system is restored to an initial state. Specifically, the correction method provided by the present embodiment is as follows.

1. The basic idea of the correction method provided by the present embodiment is to use the Monte Carlo method to adjust the distortion degree of an image.

When a radioactive source does not have a larger specificity, it can be considered that the probability that the gamma photons fall on each crystal is basically the same, and the energy distribution is basically the same. Gamma photons are scattered on the surface of the crystal as in a Monte Carlo pointing method. If the relationship and the coverage range between the detector and the scintillator are fixed, when the gain value of the detector is fixed, the number of statistical samples which reaches a certain amount will certainly reflect the intrinsic nature of the detector according to the law of large numbers.

Taking a modularized detector for example, four photo multiplier tubes occupy four quadrants of an array composed of scintillator crystals, respectively. The four quadrants are geometrically strictly symmetric. If the crystal's light yield is basically the same, the total energy under the large statistic of the four quadrants can be considered to be the same or reflects a fixed proportion relationship when the sample is large enough. Then, the total energy output by each detector under the large statistic should be the same. If the light output is inconsistent, the proportion relationship of the total energy should be fixed.

If the system can adjust the relative proportions of the four detectors in an initial state to be consistent, or adjust the same to a fixed proportion, the stability of the gains of the four detectors can be ensured, thus ensuring the stability, i.e., an image analyzed by the whole module using a centroid method does not distort, thereby ensuring that a lookup table generated by the system and used to segment the crystal is accurate and valid over a long period of time.

However, this adjustment can only ensure that the shapes of images analyzed by the four detectors will not change. If the overall energy of the module per se drifts, it is not enough to only know the relative proportion of the gains of the four detectors.

2. The drift of the overall energy is corrected using a combined peak position of the module rather than an individual peak position: although the module resolution as a whole is poor, what really needs attention is actually a center value of the peak position. The center value of the peak position is used as an absolute reference for the overall drift of the overall gain value of the module so that the gain value of the module can be adjusted.

Figure 2:
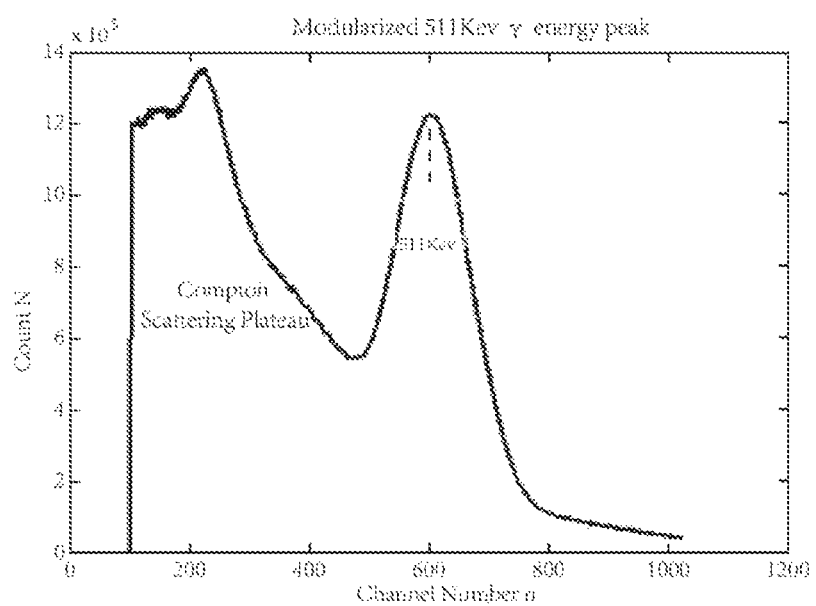
FIG. 2 is an energy peak diagram of a 511 kev Gamma photon detected by the whole module.

A peak position of a 511 kev energy peak can be seen clearly from an energy peak diagram of a 511 kev gamma photon of the whole module in FIG. 2.

3. Automatic adjustment is implemented using self-decay of a scintillator containing a radioactive isotopes: if the correction can be performed only through the radioactive source, real-time adjustment cannot be achieved under the influences of the radioactive source placement position, human error and other factors.

Figure 3:
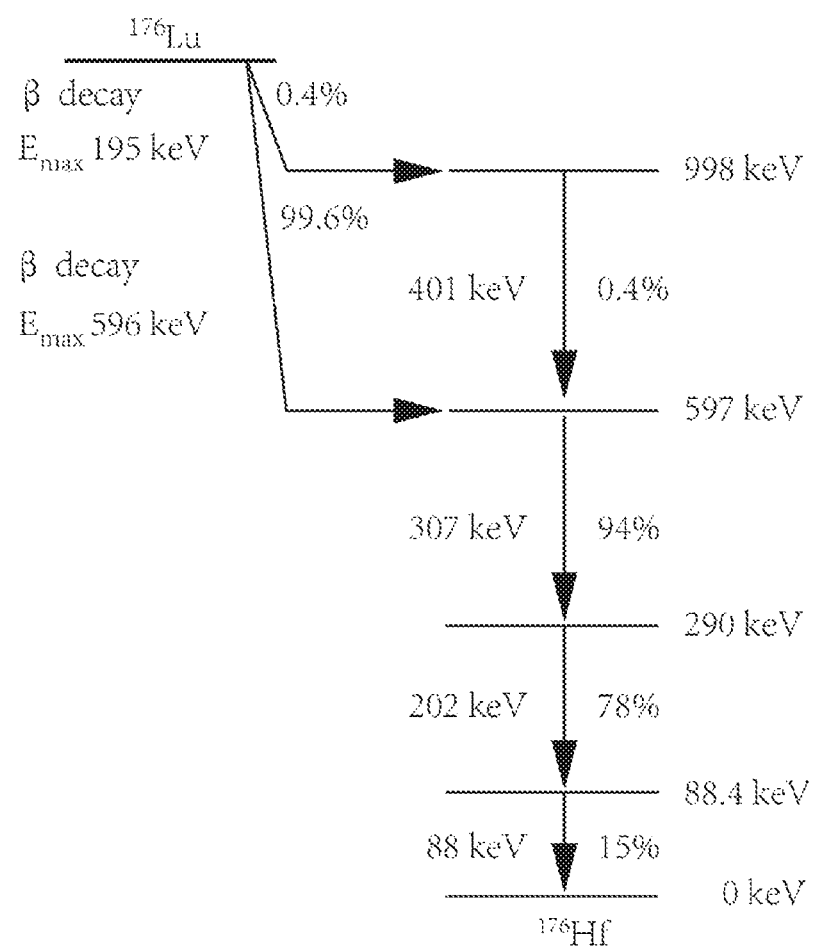
FIG. 3 is a decay energy level diagram of $^{176}$Lu.
Figure 4:
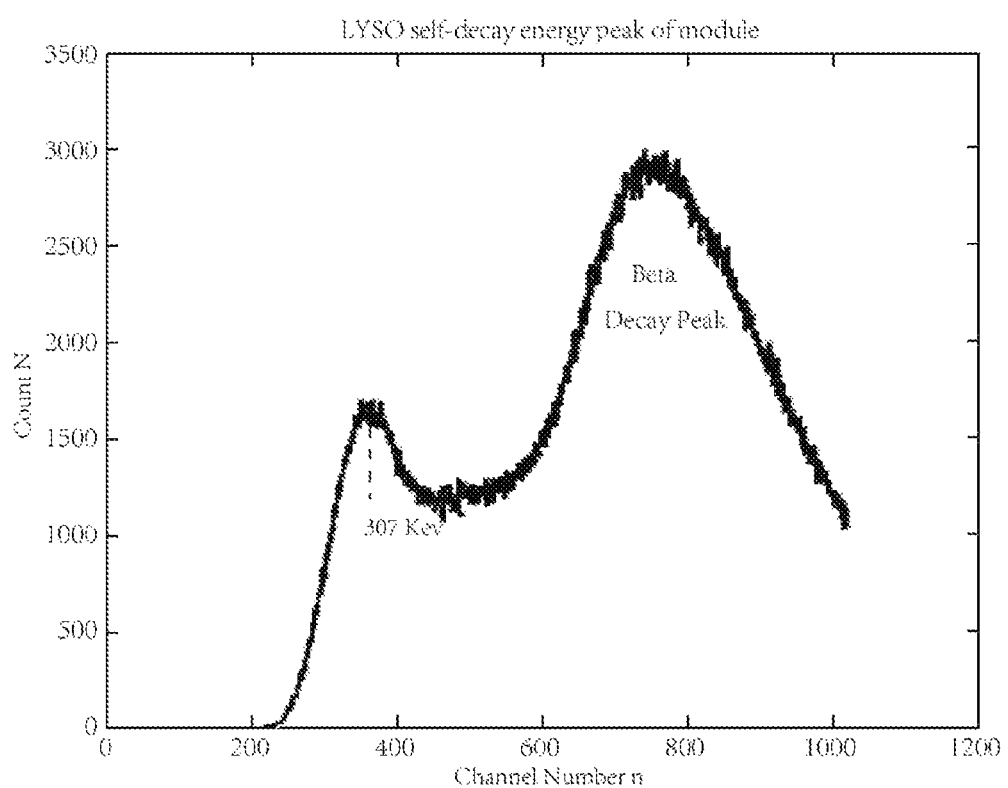
FIG. 4 is an energy spectrum diagram generated by $^{176}$Lu self-decay in an LYSO crystal of the module.

At present, there is a kind of scintillators among the scintillators used in the PET detector system that contain radioactive isotopes. This kind of scintillators that contain the radioactive isotopes also produce gamma photons during the self-decay. For example, in an LYSO scintillation crystal, it can be seen from a decay energy level diagram of $^{176}$Lu in FIG. 3 that $^{176}$Lu can undergo Beta negative decay once with a probability of 99.6%, thereby becoming $^{176}$Hf. After decay, the $^{176}$Hf in an excited state has a probability of 94% to release a 307 kev gamma photon and transitions to a 290 kev level. It can be seen from an energy spectrum of $^{176}$Lu self-decay in the LYSO crystal of the module shown in FIG. 4 that there is a significant energy peak generated by back-excitation in the vicinity of 307 keV.

The radioactive isotope in the scintillator has a long decay cycle. For example, $^{176}$Lu has a decay cycle of 2.2 billion years and the decay-induced counts are extremely stable over several decades. Although the decay of the radioactive isotope in the scintillator will increase the local noise to the PET detector system, this steady decay provides a self-correcting way for self-correction of the system.

If the content of radioactive isotope elements (such as a lutecium element) in each scintillator remains the same and the placement position relationship of the detector crystal does not change, the self-decay counts detected by each detector should be fixed throughout the life cycle. The self-correction of the system can be also realized using the self-decay of the scintillator that contains the radioactive isotope.

For Lu, it can be seen from the decay energy level that 94% of $^{176}$Lu can produce a 307 kev energy, which means that there is a significant peak position at 307 kev. The peak position generated by the self-decay of the system is shown in the figure above. It can be seen that there is a significant peak of 307 kev at a channel 360.

It may be understood by those skilled in the art that in the energy spectrum diagram, the changes of the peak position of the full-energy peak generated by the self-decay of the scintillator containing the radioactive isotope and the peak position of 511 kev are synchronized. That is, the peak position of the full-energy peak generated by the self-decay in the energy spectrum may also change when the gain value of the PET detector system changes. If the peak position of the full-energy peak of the PET detector system under the condition of self-decay is adjusted to an initial state of a system scale, the peak position of 511 kev can also be restored to an initial state, such that the system restores to a working state of a factory scale.

Based on the above-mentioned principle, the correction method provided by the present embodiment includes the following steps.

In Step 201, an initial channel number of a peak position of a full-energy peak generated by self-decay of a scintillator containing a radioactive isotope in the PET detector system, in an initial energy spectrum diagram of the PET detector system, i.e., a target total peak position of the module, is acquired.

In the present embodiment, the scintillator containing the radioactive isotope is a scintillator whose constituent atoms undergo self-decay. Specifically, the scintillator containing the radioactive isotope is a scintillator containing $^{176}$Lu or a scintillator containing $^{138}$La. The scintillator containing $^{176}$Lu may be a scintillation crystal containing $^{176}$Lu, such as a LSO scintillation crystal or an LYSO scintillation crystal, or may be a non-crystal containing $^{176}$Lu, such as LuAG or LuAP. The scintillation crystal containing $^{138}$La may be a crystal containing $^{138}$La, for example, a LaBr crystal, or may be other non-crystal containing $^{138}$La.

Taking a scintillator containing $^{176}$Lu as an example, the full-energy peak generated by the self-decay thereof can be a full-energy peak of 307 Kev or a full-energy peak of 202 Kev.

For a definite PET detector system, the initial channel number, of the peak position of the full-energy peak generated by the self-decay of a scintillator containing a radioactive isotope in the initial energy spectrum is a constant value that is related to a gain value of the PET detector system leaving from a factory. Those skilled in the art can obtain the initial channel number of the peak position of the full-energy peak generated by the self-decay of a scintillator containing a radioactive isotope in the initial energy spectrum by referring to the related information of the PET detector system leaving from a factory. It is also possible to read the initial channel number of the peak position of the full-energy peak directly from the initial energy spectrum diagram when the gain value of the PET detector system does not change.

It should be noted that a scintillator containing a radioactive isotope may produce a plurality of full-energy peaks during the self-decay. For example, a self-decay of a scintillator containing $^{176}$Lu may produce full-energy peaks of 307 Kev and 202 Kev. In the present embodiment, a full-energy peak can be taken as a research object, that is, the initial channel number of a full-energy peak is used as the target total peak position of the module. It is also possible to take the sum or the average of the plurality of full-energy peaks as a research object, that is, the sum or an average of the initial channel number of the plurality of full-energy peaks is taken as a target total peak position of the module. When the average of the plurality of full-energy peas is taken as a research object, the average can be an arithmetic average of the plurality of full-energy peaks, or a weighted average of the plurality of the full-energy peaks.

In Step 202, a ratio of an initially accumulated energy of each signal channel to a total initially accumulated energy of all of the signal channels in the PET detector system, i.e., a proportion of the target energy of each signal channel to the total energy is acquired.

The same as the initial channel number of the peak position of the full-energy peak generated by the self-decay of the scintillator containing the radioactive isotope, for a definite PET detector system, a ratio of the initially accumulated energy of each signal channel to the total initially accumulated energy of all signal channels is also a fixed value which is related to an original design of the PET detector. For example, a certain PET detector system includes four photomultiplier tubes, that is, has four signal channels. If the four signal channels are symmetrically arranged, the proportion of the target energy of each signal channel to the total energy is 0.25. If a PET detector system consists of two symmetrically arranged photomultiplier tubes, the proportion of the target energy of each signal channel to the total energy is 0.5.

It can be understood by those skilled in the art that: when the correction is performed using the correction method provided by the present embodiment, it is not necessary to perform the above steps 201 to 202 for each correction. It is possible to obtain the target total peak position of the module and the proportion of the target energy of each signal channel to the total energy only when the first correction is performed, then store the two parameters and directly use the same in the subsequent correction. In addition, the specific sequence of the above steps 201 and 202 is not limited strictly, and may be performed in a certain sequence, or may be performed simultaneously.

In Step 203, a drifted channel number of a full-energy peak position generated by self-decay of a scintillator containing a radioactive isotope in a drifted energy spectrum diagram, in a PET detector system after a gain value of the PET detector system has changed, i.e., a current total peak position of a module, is acquired.

The current total peak position of the module may also be directly read from the drifted energy spectrum.

Similar to the Step 201, in the present embodiment, a full-energy peak, or a sum or an average of a plurality of full-energy peaks may also be used as a research object, wherein when the average of the plurality of full-energy peaks is used as a research object, it can be an arithmetic average of the plurality of full-energy peaks or a weighted average of the plurality of full-energy peaks.

Specifically, a possible specific implementation manner of the Step 203 is as follows: accumulating energies of all of the self-decay cases to form an energy spectrum after the gain value of the PET detector system has changed; and acquiring, according to the energy spectrum, a drifted channel number of a peak position of a full-energy peak generated by self-decay of a scintillator containing a radioactive isotope in a drifted energy spectrum in the PET detector system, after a gain value of the PET detector system has changed, i.e., a current total peak position of a module.

Another possible specific implementation manner of the Step 203 is as follows: accumulating energies of all of the self-decay cases in a preset region to form an energy spectrum after the gain value of the PET detector system has changed; acquiring, according to the energy spectrum, a drifted channel number of peak positions of a plurality of full-energy peaks generated by self-decay of a scintillator containing a radioactive isotope in the PET detector system in a drifted energy spectrum after the gain value of the PET detector system has changed; and calculating a sum or an average of the drifted channel number of the peak positions of the plurality of full-energy peaks to obtain a current total peak position of the module. The average may be an arithmetic average or a weighted average.

It may be understood by those skilled in the art that the research object in step 203 should correspond to the research object in step 201. Taking a scintillator containing $^{176}$Lu as an example, when the peak position of 307 Kev is selected as the research object in step 201, the drift channel number of 307 Kev should also be taken as the current total peak position of the module in step 203. When the sum of 307 Kev and 202 Kev is selected as the research object in step 201, the sum of the drift channel number of 307 Kev and the drift channel number of 202 Kev should also be taken as the current total peak position of the module in step 203.

In Step 204, a ratio of a currently accumulated energy of each signal channel to a total currently accumulated energy of all signal channels in the PET detector system, i.e., a proportion of the current energy of each signal channel to a total energy, after the gain value of the PET detector system has changed is acquired.

A possible specific implementation manner of the Step 204 is as follows.

In Step 2041, a plurality of self-decay cases of the scintillator containing the radioactive isotope in the PET detector system after the gain value of the PET detector system has changed is collected.

According to the above explanation of the principle of the correction method provided by the present embodiment, the intrinsic property of the detector can be reflected only when the number of statistical samples reaches a certain value. Therefore, the number of self-decay cases obtained in this step should be as much as possible, so that the value of a proportion of the resulting current energy of each signal channel to the total energy is more accurate. However, if the number of collected self-decay cases is too large, the cycle of one correction will be prolonged. Therefore, the number of the collected self-decay cases is preferably from 100,000 to 200,000, for example, it may be 120,000, 140,000, 150,000, 160,000, 180000 and the like.

In Step 2042, a currently accumulated energy of each signal channel in the plurality of self-decay cases of the scintillator containing the radioactive isotope is calculated.

In Step 2043, a total currently accumulated energy of all signal channels in the plurality of self-decay cases of the scintillator containing the radioactive isotope is calculated.

In Step 2044, a ratio of the currently accumulated energy of each signal channel to the total currently accumulated energy of all signal channels, i.e., a proportion of the current energy of each signal channel to the total energy, in the plurality of self-decay cases of the scintillator containing the radioactive isotope is calculated.

Another possible specific implementation manner of Step 204 is as follows:

In Step 2041', a plurality of self-decay cases of the scintillator containing the radioactive isotope in the PET detector system after the gain value of the PET detector system has changed is collected.

In Step 2042', a currently accumulated energy of each signal channel which pass through a present energy window in a preset region in the plurality of self-decay cases of the scintillator containing the radioactive isotope is calculated. Taking the PET detector system shown in FIG. 5 as an example, the preset region may be a region covered by a detector A, or may be a region covered by a detector B or a detector C or a detector D. The preset energy window can be between 100 kev and 750 kev.

In Step 2043', a total currently accumulated energy of all of the signal channels which pass through the present energy window in the region in the plurality of self-decay cases of the scintillator containing the radioactive isotope is calculated.

In Step 2044', a ratio of the currently accumulated energy of each signal channel to the total currently accumulated energy of all signal channels, i.e., a proportion of the current energy of each signal channel to the total energy, in the plurality of self-decay cases of the scintillator containing the radioactive isotope is calculated.

In Step 205, the current total peak position of the module, the proportion of the current energy of each signal channel to the total energy, a target total peak position of the module, and the proportion of a target energy of each signal channel to the total energy acquired in Steps 201 to 204 are substituted into the following formula to calculate a gain adjustment ratio of each signal channel:

$$A(x) = \frac{Pref * Gref(x)}{Pcur * Gcur(x)},$$

wherein, x represents a signal channel number which is an integer from 1 to N, and N is a total signal channel number in the PET detector system; $A(x)$ is a gain adjustment ratio of a signal channel x; $Pref$ is a target total peak position of the module; $Gref(x)$ is a proportion of a target energy of the signal channel x to a total energy; $Pcur$ is a current total peak position of the module; $Gcur(x)$ is a proportion of the current energy of the signal channel x to the total energy.

In Step 206, gain adjustment is performed for each signal channel respectively according to the gain adjustment ratio of each signal channel.

It can be understood by those skilled in the art that, after calculating the gain adjustment ratio of each signal channel, the current gain value of each signal channel is adjusted with a corresponding multiple to restore the gain value of each channel to an initial state. For example, if the gain adjustment ratio of a signal channel is calculated to be 1.5, the signal channel can be restored to the initial state after the gain value of the signal channel is adjusted to 1.5 times of the current gain value. Similarly, if the gain adjustment ratio of a signal channel is calculated to be 0.5, the signal channel can be restored to the initial state after the gain value of the signal channel is adjusted to 0.5 times of the current gain value.

Figure 9:
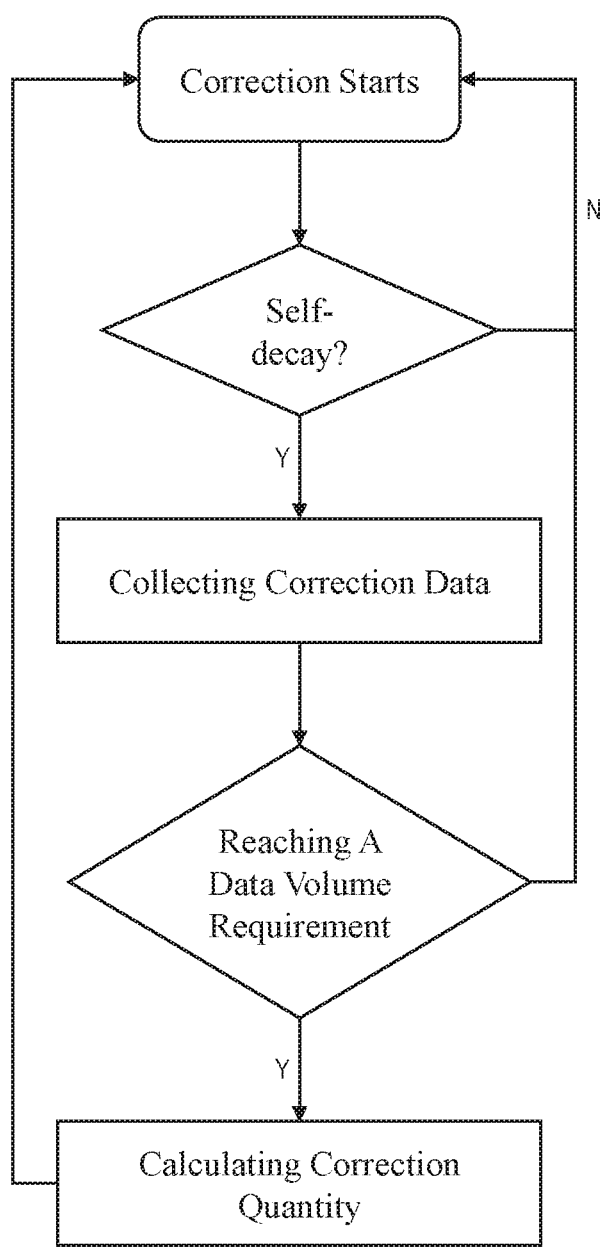
FIG. 9 is a flowchart of online real-time adjustment.

In practice, the PET detector system can be adjusted on line in real time according to a flowchart as shown in FIG. 9.

First, the PET detector detects whether the PET detector system is in a self-decay state (i.e., it is not in a working state for testing a patient) every a predetermined time interval. If it is detected that the PET detector system is in a state of only self-decay, the above steps 203 to 206 are started to collect the data required for the correction process. After the amount of collected data reaches a correction requirement, one correction is completed (if the correction method of the present embodiment is used for correction for the first time, the above steps 201 to 206 are completely performed).

In addition, in order to reduce the workload of correction, it is possible to set a threshold range for a difference between the current total peak position of a module and the target total peak position of the module. After step 203 is performed, that is, after the current total peak position of the module is acquired, the current total peak position of the module is compared with the target total peak position of the module obtained in step 201. If the difference therebetween is within the threshold range, it is indicated that the gain value of the PET detector system is not changed significantly and has little effect on the accuracy of the test result. In this case, the subsequent steps 204 to 206 may not be performed. When the difference between the current total peak position of the module and the target total peak position of the module is beyond the threshold range, it is indicated that the gain value of the PET detector system changes more significantly and needs to be corrected, and steps 204 to 206 are then continued to finish the correction.

From the above, the correction method provided by the present embodiment uses the Monte Carlo method to accumulate a certain number of random numbers to calculate the relative proportion of the gain of each signal channel for decoding a crystal array, uses the modularized peak position to determine the gain change of the whole module and use the self-decay characteristics of radioactive isotope, such as $^{176}$Lu or $^{138}$La to achieve real-time adjustment of the system. Therefore, the correction method provided in the present disclosure has the following advantages.

1. Few parameters are involved for the adjustment, for example a module that analyzes an array through four channels of signals only needs to determine five parameters to perform online real-time correction and adjustment. In addition, these five parameters are independent of each other and reflect the nature of the parameters corresponding to their own.

2. Fewer parameters mean fewer data samples and faster adjustment speed. It can be found upon experiments that once adjustment can be achieved just by less than 10 seconds of data. It also means simpler implementation, lower probability of errors, and lower detection and maintenance costs.

3. The system can be automatically adjusted by means of a self-decay effect of the scintillator containing the radioactive isotope in the PET system without a radioactive source state.

Figure 5:
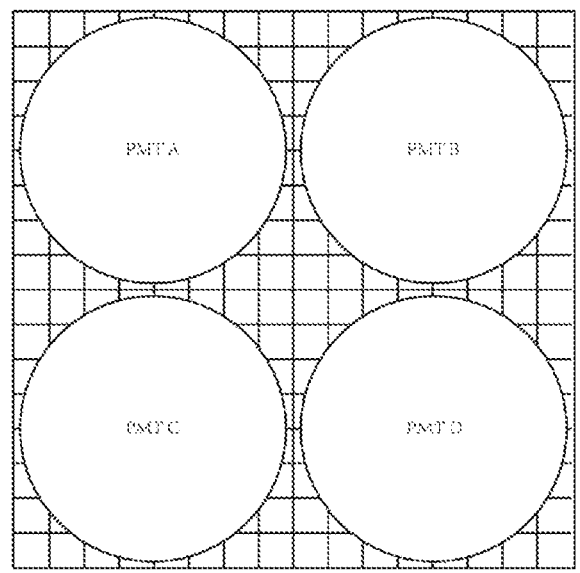
FIG. 5 is a schematic diagram of the module that uses four channels of signals to analyze an array.

In the present embodiment, the correction method provided by the present embodiment of the present disclosure is further illustrated by taking a PET detector system shown in FIG. 5 as an example. As shown in FIG. 5, a 16×16 crystal array is read out by four channels of PMT through a shaped amplification circuit and digitization. An image of the 16×16 array is analyzed out using a centroid method.

A crystal containing a lutetium element, which is used in the PET detector system is LYSO crystal.

A method for correcting the PET detector system includes the following steps.

In Step 401, an initial channel number of a 307 kev initial peak position generated by $^{176}$Lu self-decay of an LYSO crystal in the PET detector system in an initial energy spectrum diagram, i.e., a target total peak position of the module, is acquired.

A ratio of an initially accumulated energy of each signal channel to a total accumulated energy of all of the initial signal channels in the PET detector, i.e., a proportion of a target energy of the signal channel x to the total energy, is acquired.

Figure 7:
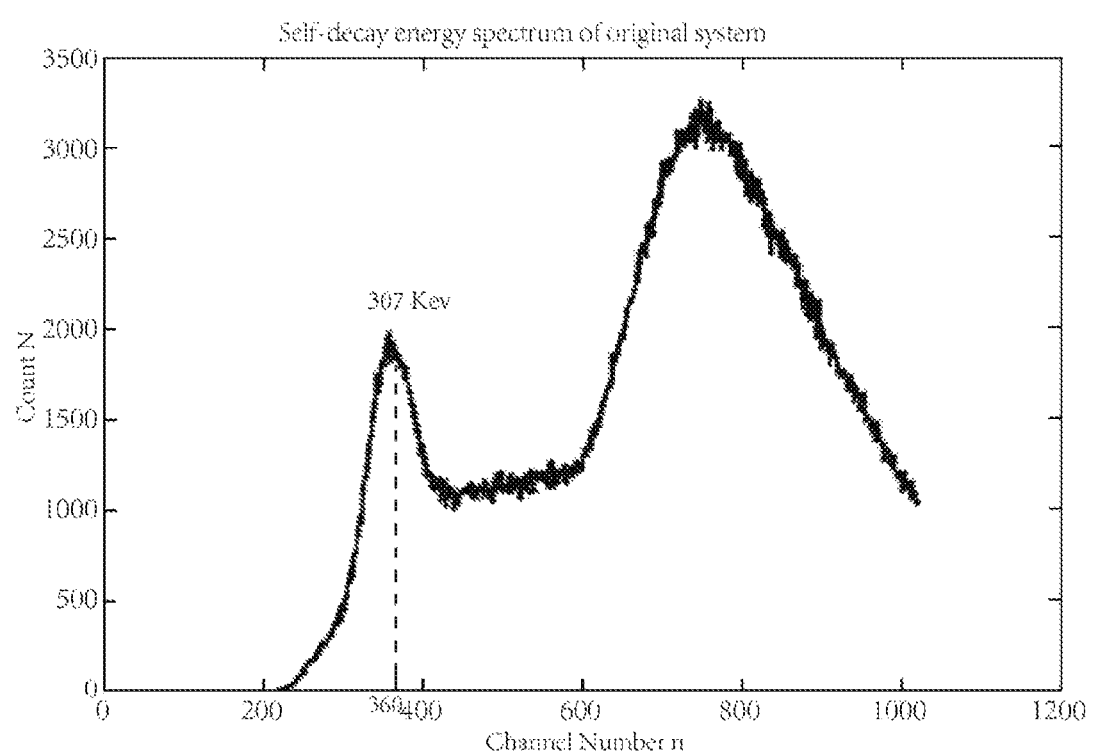
FIG. 7 is a self-decay energy spectrum diagram of an initial system.

As can be seen from a self-decay energy spectrum diagram of an initial system in FIG. 7: the initial peak position of 307 kev generated by the self-decay of the LYSO crystal is on a channel number of Pref=360.

As shown in FIG. 5, the four PMTs in the PET detector system are symmetrically arranged, that is, the four signal channels are symmetrically arranged. Therefore, a proportion of the target energy in the signal channel x (x=1, 2, 3, or 4) to the total energy is as follows: Gref(1)=0.25; Gref (2)=0.25; Gref(3)=0.25; Gref(4)=0.25, wherein x=1 corresponds to a signal channel corresponding to PMT A, x=2 corresponds to a signal channel corresponding to PMT B, x=3 corresponds to a signal channel corresponding to PMT C, and x=4 corresponds to a signal channel corresponding to PMT D, similarly hereinafter.

In Step 402, a drifted channel number of a 307 kev initial peak position which is generated by $^{176}$Lu self-decay of the LYSO crystal in the PET detector system, in a drifted energy spectrum, i.e., a current total peak position of the module, is acquired.

After acquiring a plurality of LYSO self-decay cases collected randomly, the PET detector system calculates and outputs an accumulated energy of each signal channel in the plurality of LYSO self-decay cases; and calculates a current ratio of an accumulated energy of each signal channel to the total accumulated energy of all signal channels, i.e., a proportion of the current energy of the signal channel x to a total energy, in the plurality of LYSO self-decay cases respectively.

After collecting 100,000 LYSO self-decay cases, the system accumulates the energy for the four signal channels in these cases and calculates a total energy of the signal channel A as 14036116, the total amount of the signal channel B as 16477179, the total energy of the signal channel C as 13425850, and the total energy of the signal channel D as 17087445. The total energy of the whole detector module is 61026590.

Therefore, a proportion of the current energy of the signal channel x to the total energy is: Gcur(1)=14036116/61026590≈0.23; Gcur(2)=16477179/61026590≈0.27; Gcur(3)=13425850/61026590≈0.22; Gcur(4)=17087445/61026590≈0.28.

As a region over against the PMT is closer to a channel, in order to further improve the accuracy of the accumulated energy of the channel, it is possible to accumulate cases in the region over against the PMT. Those Cases of crystals far from the PMT are screened out.

Figure 8:
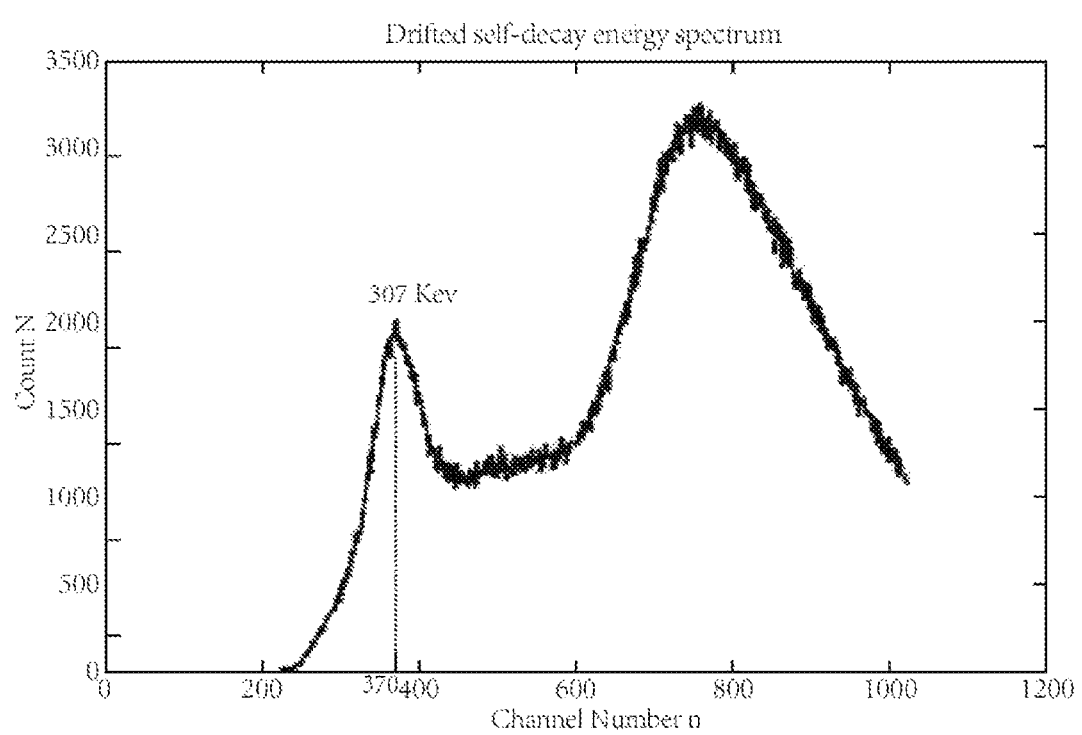
FIG. 8 is a self-decay energy peak diagram of a drifted system.

As can be seen from the self-decay energy peak diagram of the system after drift shown in FIG. 8: an energy peak of 307 kev drifts to a channel number of Pcur=370.

In Step 403, a gain adjustment ratio of each signal channel is calculated according to the following formula:

$$A(x) = \frac{Pref * Gref(x)}{Pcur * Gcur(x)},$$

wherein, A(x) is a gain adjustment ratio of a signal channel x; Pref is a target total peak position of the module; Gref(x) is a proportion of a total energy of the signal channel x to a total energy; Pcur is a current total peak position of the module; Gcur(x) is a proportion of the current energy of the signal channel x to the total energy.

Specifically, the gain adjustment ratio A (1) of the signal channel A, the gain adjustment ratio A (2) of the signal channel B, the gain adjustment ratio A (3) of the signal channel C and the gain adjustment ratio A (4) of the signal channel D are calculated respectively according to the following formulas:

$$A(1) = \frac{Pref \times Gref(1)}{Pcur \times Gcur(1)};$$

$$A(2) = \frac{Pref \times Gref(2)}{Pcur \times Gcur(2)};$$

$$A(3) = \frac{Pref \times Gref(3)}{Pcur \times Gcur(3)};$$

$$A(4) = \frac{Pref \times Gref(4)}{Pcur \times Gcur(4)}.$$

$A(1)=(360*0.25)/(370*0.23)≈1.058;$ $A(2)=(360*0.25)/(370*0.27)≈0.901;$ $A(3)=(360*0.25)/(370*0.22)≈1.106;$ $A(4)=(360*0.25)/(370*0.28)≈0.869.$

In Step 404, gain adjustment is performed for each signal channel respectively according to the gain adjustment ratio of each signal channel.

According to the above coefficients, the gain of each signal of A, B, C and D is readjusted: the gain of the signal channel A is adjusted to 1.058 times of the current one; the gain of the signal channel B is adjusted to 0.901 times of the current one; the gain of the signal channel C is adjusted to 1.106 times of the current one; the gain of the signal channel D is adjusted to 0.869 times of the current one. After repeated iterations, the system is restored to its original state.

Figure 6:
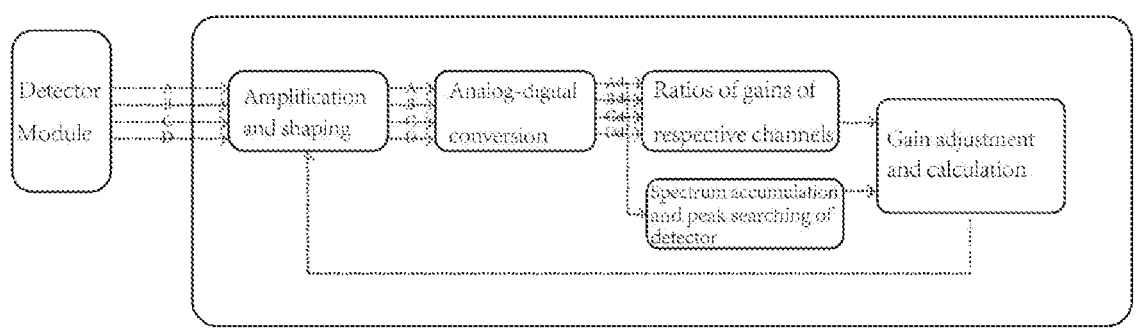
FIG. 6 is a working schematic diagram of online real-time correction for a positron emission tomography (PET) detector.

FIG. 6 illustrates a working principle of online real-time correction for a positron emission tomography (PET) detector. As can be seen from FIG. 6, the detector module sends four signals A, B, C and D into a signal processing board. The signals are amplified and shaped by the signal processing board and are then sent into an analog-digital conversion device to be converted into digital signals. Ratios of gains of respective channel signals are calculated for the digital signals. A new gain adjustment coefficient of each channel is obtained in combination with a peak searching module and then output for adjusting the gain of an amplifying and shaping module, thereby achieving the purpose of stabilizing the detector signals.

Figure 10:
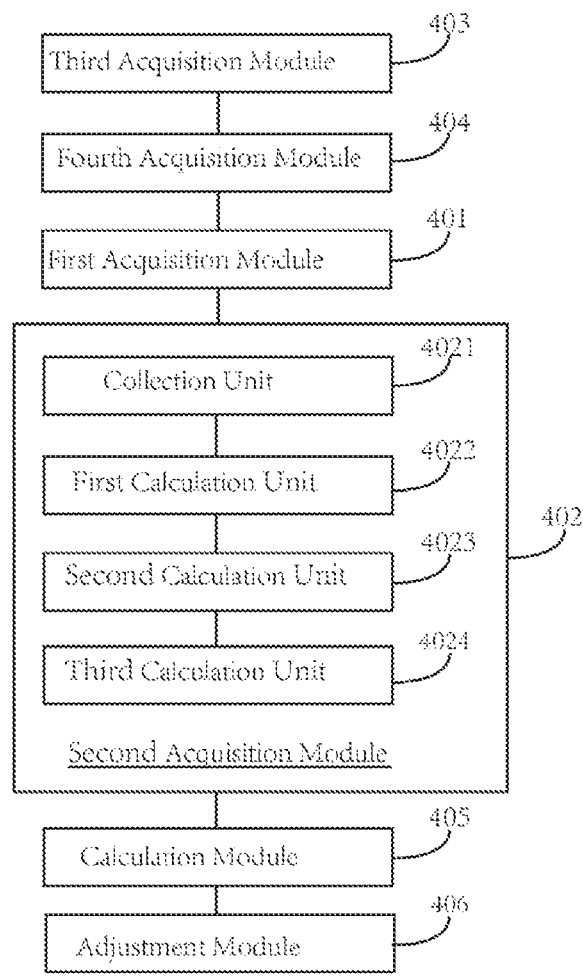
FIG. 10 is a schematic diagram of an online real-time correction system for the PET detector provided by an embodiment of the present disclosure.

The present embodiment of the present disclosure provides an online real-time correction system for a positron emission tomography (PET) detector. Referring to FIG. 10, the correction system includes a first acquisition module 401, a second acquisition module 402, a calculation module 405 and an adjustment module 406. The first acquisition module 401 is configured to acquire a drifted channel number of a peak position of a full-energy peak generated by self-decay of a scintillator containing a radioactive isotope in the PET system in a drifted energy spectrum diagram after a gain value of the PET detector system has changed, i.e., a current total peak position of a module. The second acquisition module 402 is configured to acquire a ratio of a currently accumulated energy of each signal channel to a total currently accumulated energy of all signal channels in the PET detector system, after the gain value of the PET detector system has changed, i.e., a proportion of the current energy of each signal channel to a total energy. The calculation module 405 is configured to substitute the current total peak position of the module, the proportion of the current energy of each signal channel to the total energy and a target total peak position of the module, and the proportion of a target energy of each signal channel to the total energy into the following formula to calculate a gain adjustment ratio of each signal channel:

$$A(x) = \frac{Pref * Gref(x)}{Pcur * Gcur(x)},$$

wherein, x represents a signal channel number which is an integer from 1 to N, and N is a total signal channel number in the PET detector system; A(x) is a gain adjustment ratio of a signal channel x; Pref is a target total target peak position of the module; Gref(x) is a proportion of a target energy of the signal channel x to a total energy; Pcur is a current total peak position of the module; Gcur(x) is a proportion of the current energy of the signal channel x to the total energy; the total target peak position of the module is an initial channel number of a peak position of a full-energy peak which is generated by self-decay of the scintillator containing the radioactive isotope in the PET detector system, in an initial energy spectrum diagram; the proportion of the target energy of each signal channel to the total energy is a ratio of an initially accumulated energy of each signal channel to a total initially accumulated energy of all of the signal channels in the PET detector system. The adjustment module 406 is configured to perform gain adjustment for each signal channel respectively according to the gain adjustment ratio of each signal channel.

Optionally, the first acquisition module 401 is specifically configured to: accumulate energies of all the self-decay cases to form an energy spectrum after a gain value of the PET detector system has changed; and acquire, according to the energy spectrum, a drifted channel number of a peak position of a full-energy peak which is generated by self-decay of a scintillator containing a radioactive isotope in the PET detector system, in a drifted energy spectrum after the gain value of the PET detector system has changed.

Optionally, the first acquisition module 401 is specifically configured to: accumulate energies of all the self-decay cases in a preset region to form an energy spectrum after a gain value of the PET detector system has changed; acquire, according to the energy spectrum, drifted channel numbers of peak positions of a plurality of full-energy peaks which is generated by self-decay of a scintillator containing a radioactive isotope in the PET detector system, in a drifted energy spectrum diagram after the gain value of the PET detector system has changed; and calculate a sum or an average of the drifted channel numbers of the peak positions of the plurality of full-energy peaks to obtain the current total peak position of the module.

Further, the second acquisition module 402 includes a collection unit 4021, a first calculation unit 4022, a second calculation unit 4023 and a third calculation unit 4024. The collection unit 4021 is configured to collect a plurality of self-decay cases of the scintillator containing the radioactive isotope in the PET detector system after the gain value of the PET detector system has changed. The first calculation unit 4022 is configured to calculate the currently accumulated energy of each signal channel in the plurality of self-decay cases of the scintillator containing the radioactive isotope. The second calculation unit 4023 is configured to calculate the total currently accumulated energy of all of the signal channels in the plurality of self-decay cases of the scintillator containing the radioactive isotope. The third calculation unit 4024 is configured to calculate the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

Optionally, the collection unit 4021 is configured to acquire the plurality of self-decay cases of the scintillator containing the radioactive isotope in the PET detector system after the gain value of the PET detector system has changed. The first calculation unit 4022 is configured to calculate the currently accumulated energy of each signal channel which passes through a present energy window in a preset region in the plurality of self-decay cases of the scintillator containing the radioactive isotope. The second calculation module 4023 is configured to calculate a total currently accumulated energy of all of the signal channels which pass through the present energy window in the region in the plurality of self-decay cases of the scintillator containing the radioactive isotope. The third calculation unit 4024 is configured to calculate the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

Further, the correction system provided by the present embodiment further includes a third acquisition module 403 and a fourth acquisition module 404. The third acquisition module 403 is configured to acquire the initial channel number of the peak position of the full-energy peak which is generated by self-decay of the scintillator containing the radioactive isotope in the PET detector system, in an initial energy spectrum diagram of the PET detector system, i.e., the target total peak position of the module. The fourth acquisition module 404 is configured to acquire the ratio of the initially accumulated energy of each signal channel to the total initially accumulated energy of all of the signal channels in the PET detector system, i.e., the proportion of the target energy of each signal channel to the total energy.

Further, the scintillator containing the radioactive isotope is a scintillator whose constituent atoms undergo self-decay. The scintillator containing the radioactive isotope is a scintillator containing $^{176}$Lu or a scintillator containing $^{138}$La. Specifically, the scintillator containing $^{176}$Lu may be a scintillation crystal containing $^{176}$Lu, such as a LSO scintillation crystal or an LYSO scintillation crystal, or may be a non-crystal containing $^{176}$Lu, such as LuAG or LuAP. The scintillator containing $^{138}$La may be a crystal containing $^{138}$La, for example, a LaBr crystal, or may be other non-crystal containing $^{138}$La.

Further, in the correction system provided by the present embodiment of the present disclosure, the third acquisition module 403 is configured to acquire the initial channel number of the peak position of the full-energy peak which is generated by self-decay of the scintillator containing the radioactive isotope in the PET detector system, in an initial energy spectrum diagram, i.e., the target total peak position of the module. The fourth acquisition module 404 is configured to acquire the ratio of the initially accumulated energy of each signal channel to the total accumulated energy of all of the signal channels in the PET detector system, i.e., the proportion of the target energy of the signal channel x to the total energy. The first acquisition module 401 is configured to acquire a drifted channel number of a peak position of a full-energy peak which is generated by self-decay of the scintillator containing the radioactive isotope in the PET detector system, in a drifted energy spectrum diagram, i.e., the current total peak position of the module. The second acquisition module 402 is configured to: calculate and output, after acquiring, by the PET detector system, a plurality of self-decay cases of the scintillator collected randomly, the accumulated energy of each signal channel in the plurality of self-decay cases of the scintillator; and calculate the current ratio of the accumulated energy of each signal channel to the total accumulated energy of all signal channels, i.e., the proportion of the current energy of the signal channel x to the total energy, in the plurality of self-decay cases of the scintillator. The calculation module 405 is configured to calculate a gain adjustment ratio of each signal channel respectively according to the following formula:

$$A(x) = \frac{Pref * Gref(x)}{Pcur * Gcur(x)};$$

in which x is an integer larger than or equal to 4; A(x) is the gain adjustment ratio of the signal channel x; Pref is the target total peak position of the module; Gref(x) is the proportion of the target energy of the signal channel x to the total energy; Pcur is the current total peak position of the module; Gcur(x) is the proportion of the current energy of the signal channel x to the total energy. The adjustment module 406 is configured to, perform gain adjustment for each signal channel respectively according to the gain adjustment ratio of each signal channel.

Further, in the correction system provided by the present embodiment, the third acquisition module 403 is configured to acquire an initial channel number of a 307 kev initial peak position which is generated by $^{176}$Lu self-decay of an LYSO crystal in the PET detector system, in the initial energy spectrum diagram, i.e., the total peak position of the module. The fourth acquisition module 404 is configured to acquire the ratio of the initially accumulated energy of each signal channel to the total accumulated energy of all of the initial signal channels in the PET detector, i.e., the proportion of the target energy of the signal channel x to the total energy. The first acquisition module 401 is configured to acquire a drifted channel number of a 307 kev initial peak position which is generated by $^{176}$Lu self-decay of the LYSO crystal in the PET detector system, in a drifted energy spectrum diagram, i.e., the current total peak position of the module. The second acquisition module 402 is configured to: calculate and output, after acquiring, by the PET detector system, a plurality of LYSO self-decay cases collected randomly, the accumulated energy of each signal channel in the plurality of LYSO self-decay cases; and calculate the current ratio of the accumulated energy of each signal channel to the total accumulated energy of all signal channels, i.e., the proportion of the current energy of the signal channel x to the total energy, in the plurality of LYSO self-decay cases respectively. The calculation module 405 is configured to calculate the gain adjustment ratio of each signal channel respectively according to the following formula:

$$A(x) = \frac{Pref * Gref(x)}{Pcur * Gcur(x)};$$

in which, x is an integer larger than or equal to 4; A(x) is the gain adjustment ratio of the signal channel x; Pref is the target total peak position of the module; Gref(x) is the proportion of the target energy of the signal channel x to the total energy; Pcur is the current total peak position of the module; Gcur(x) is the proportion of the current energy of the signal channel x to the total energy. The adjustment module 406 is configured to, perform gain adjustment for each signal channel respectively according to the gain adjustment ratio of each signal channel.

It should be noted that: the correction system provided by the present embodiment is only illustrated by dividing the functional modules as an example in the correction of the PET detector system. In practical applications, the above function can be completed by different function modules allocated as required, that is, the internal structure of the system is divided into different function modules to complete all or part of the functions described above. In addition, the correction system and the correction method embodiments provided by the present embodiment belong to the same concept. The specific implementation processes of the correction system refer to the method embodiments for details, and will not described herein again.

Those skilled in the art should understand that all or part of the steps of implementing the foregoing embodiments may be implemented by hardware or by instructing relevant hardware through a program. The program may be stored in a computer-readable storage medium, and the above-mentioned storage medium may be a read-only memory, a magnetic disk or an optical disk, or the like.

The above-mentioned embodiments are just preferred embodiments of the present disclosure, without limiting the present disclosure. Any modifications, equivalent replacements and improvements made within the spirit and principle of the present disclosure should be included within the protection scope of the present disclosure.

What is claimed is:

1. An online real-time correction method for a positron emission tomography (PET) detector, comprising the following steps:

a. acquiring a drifted channel number of a peak position of a full-energy peak which is generated by self-decay of a scintillator containing a radioactive isotope in a PET detector system, i.e., a current total peak position of a module, in a drifted energy spectrum diagram after a gain value of the PET detector system has changed, wherein the PET detector system comprises a plurality of photo multiplier tubes;

b. acquiring a ratio of a currently accumulated energy of each signal channel to a total currently accumulated energy of all signal channels in the PET detector system, i.e., a proportion of the current energy of each signal channel to a total energy, after the gain value of the PET detector system has changed;

c. substituting the current total peak position of the module, the proportion of the current energy of each signal channel to the total energy and a target total peak position of the module, and a proportion of a target energy of each signal channel to the total energy into the following formula to calculate a gain adjustment ratio of each signal channel:

$$A(x) = \frac{Pref * Gref(x)}{Pcur * Gcur(x)};$$

wherein, x represents a signal channel number which is an integer from 1 to N, and N is a total signal channel number in the PET detector system; A(x) is a gain adjustment ratio of a signal channel x; Pref is a target total peak position of the module; Gref(x) is a proportion of a target energy of the signal channel x to the total energy; Pcur is a current total peak position of the module; Gcur(x) is a proportion of a current energy of the signal channel x to the total energy; the target total peak position of the module is an initial channel number of the peak position of the full-energy peak which is generated by self-decay of the scintillator containing the radioactive isotope in the PET detector system, in an initial energy spectrum diagram; the proportion of the target energy of each signal channel to the total energy is a ratio of an initially accumulated energy of each signal channel to a total initially accumulated energy of all of the signal channels in the PET detector system; and d. performing, according to the gain adjustment ratio of each signal channel, gain adjustment for each signal channel respectively.

2. The correction method according to claim 1, wherein the step a. comprises:

accumulating energies of all self-decay cases to form an energy spectrum after the gain value of the PET detector system has changed; and acquiring, according to the energy spectrum, a drifted channel number of a peak position of a full-energy peak which is generated by self-decay of the scintillator containing the radioactive isotope in the PET detector system, in the drifted energy spectrum diagram after the gain value of the PET detector system has changed.

3. The correction method according to claim 1, wherein the step a. comprises:

accumulating energies of all self-decay cases in a preset region to form an energy spectrum after the gain value of the PET detector system has changed;

acquiring, according to the energy spectrum, drifted channel numbers of peak positions of a plurality of full-energy peaks which is generated by self-decay of the scintillator containing the radioactive isotope in the PET detector system, in the drifted energy spectrum diagram after the gain value of the PET detector system has changed; and calculating a sum or an average of the drifted channel numbers of the peak positions of the plurality of full-energy peaks to obtain the current total peak position of the module.

4. The correction method according to claim 1, wherein the step b. comprises:

acquiring a plurality of self-decay cases of the scintillator containing the radioactive isotope in the PET detector system after the gain value of the PET detector system has changed;

calculating the currently accumulated energy of each signal channel in the plurality of self-decay cases of the scintillator containing the radioactive isotope;

calculating the total currently accumulated energy of all signal channels in the plurality of self-decay cases of the scintillator containing the radioactive isotope; and calculating the ratio of the currently accumulated energy of each signal channel to the total currently accumulated energy of all of the signal channels, i.e., the proportion of the current energy of each signal channel to the total energy, in the plurality of self-decay cases of the scintillator containing the radioactive isotope.

5. The correction method according to claim 4, wherein the step b. comprises:

acquiring the plurality of self-decay cases of the scintillator containing the radioactive isotope in the PET detector system after the gain value of the PET detector system has changed;

calculating the currently accumulated energy of each signal channel which passes through a present energy window in a preset region in the plurality of self-decay cases of the scintillator containing the radioactive isotope;

calculating the total currently accumulated energy of all of the signal channels which pass through the present energy window in the preset region in the plurality of self-decay cases of the scintillator containing the radioactive isotope; and calculating the ratio of the currently accumulated energy of each signal channel to the total currently accumulated energy of all of the signal channels, i.e., the proportion of the current energy of each signal channel to the total energy, in the plurality of self-decay cases of the scintillator containing the radioactive isotope.

6. The correction method according to claim 1, wherein the correction method further comprises:

acquiring the initial channel number of the peak position of the full-energy peak which is generated by self-decay of the scintillator containing the radioactive isotope in the PET detector system, in the initial energy spectrum diagram of the PET detector system, i.e., the target total peak position of the module; and acquiring the ratio of the initially accumulated energy of each signal channel to the total initially accumulated energy of all of the signal channels in the PET detector system, i.e., the proportion of the target energy of each signal channel to the total energy.

7. The correction method according to claim 6, further comprising the following steps:

1) acquiring the initial channel number of the peak position of the full-energy peak which is generated by self-decay of the scintillator containing the radioactive isotope in the PET detector system, in the initial energy spectrum diagram, i.e., the target total peak position of the module;

acquiring the ratio of the initially accumulated energy of each channel to the total accumulated energy of all of the initial signal channels in the PET detector, i.e., the proportion of the target energy of the signal channel x to the total energy;

2) acquiring the drifted channel number of the peak position of the full-energy peak which is generated by self-decay of the scintillator containing the radioactive isotope in the PET detector system in the drifted energy spectrum diagram, i.e., the current total peak position of the module;

after collecting, by the PET detector system, a plurality of self-decay cases of the scintillator randomly, calculating and outputting the accumulated energy of each signal channel in the plurality of self-decay cases of the scintillator; calculating the current ratio of the accumulated energy of each signal channel to the total accumulated energy of all signal channels, i.e., the proportion of the current energy of the signal channel x to the total energy, in the plurality of self-decay cases of the scintillator respectively;

3) calculating a gain adjustment ratio of each signal channel respectively according to the following formula:

$$A(x) = \frac{Pref * Gref(x)}{Pcur * Gcur(x)},$$

in which x is an integer larger than or equal to 4;

A(x) is the gain adjustment ratio of the signal channel x;

Pref is the target total peak position of the module;
Gref(x) is the proportion of the target energy of the signal channel x to the total energy;
Pcur is the current total peak position of the module;
Gcur(x) is the ratio of the current energy of the signal channel x to the total energy; and 4) performing, according to the gain adjustment ratio of each signal channel, gain adjustment for each signal channel.

8. The correction method according to claim 7, further comprising the following steps:
1) acquiring an initial channel number of a 307 key initial peak position which is generated by 1 76Lu self-decay of an LYSO crystal in the PET detector system, in the initial energy spectrum diagram, i.e., the target total peak position of the module; acquiring the ratio of the initially accumulated energy of each channel to the total accumulated energy of all of the initial signal channels in the PET detector, i.e., the proportion of the target energy of the signal channel x to the total energy;
2) acquiring a drifted channel number of a 307 key initial peak position which is generated by 176Lu self-decay of the LYSO crystal in the PET detector system, in the drifted energy spectrum diagram, i.e., the current total peak position of the module;
after acquiring, by the PET detector system, a plurality of LYSO self-decay cases randomly, calculating and outputting the accumulated energy of each signal channel in the plurality of LYSO self-decay cases; calculating the current ratio of the accumulated energy of each signal channel to the total accumulated energy of all signal channels, i.e., the proportion of the current energy of the signal channel x to the total energy, in the plurality of LYSO self-decay cases respectively;
3) calculating a gain adjustment ratio of each signal channel respectively according to the following equation:

$$A(x) = \frac{Pref * Gref(x)}{Pcur * Gcur(x)},$$

in which, x is an integer larger than or equal to 4; A(x) is the gain adjustment ratio of the signal channel x; Pref is the total target peak position of the module; Gref(x) is the proportion of the target energy of the signal channel x to the total energy; Pcur is the current total peak position of the module; Gcur(x) is the proportion of the current energy of the signal channel x to the total energy; and
4) performing, according to the gain adjustment ratio of each signal channel, gain adjustment for each signal channel.

9. The correction method according to claim 1, wherein the scintillator containing the radioactive isotope is a scintillator whose constituent atoms undergo self-decay.

10. The correction method according to claim 9, wherein the scintillator containing the radioactive isotope is a scintillator containing 176Lu or a scintillator containing 138La.

11. The correction method according to claim 10, wherein the scintillator containing 1 76Lu is selected from a scintillation crystal containing 1 76Lu or a non-crystal containing 175Lu; the scintillator containing 138La is selected from a crystal containing 138La or a non-crystal containing 138La.

12. The correction method according to claim 11, wherein the scintillation crystal containing 176Lu is selected from an LSO scintillation crystal or an LYSO scintillation crystal; the non-crystal containing 176Lu is selected from LuAG or LuAP; the crystal containing 138La is selected from a LaBr crystal.

13. An on-line real-time correction system for a positron emission tomography (PET) detector, comprising:
at least a processor; and
at least a computer readable storage medium containing instructions of programs executed by the processor, wherein the instructions comprises:
a first acquisition module, a second acquisition module, a calculation module and an adjustment module, wherein the first acquisition module is configured to acquire a drifted channel number of a peak position of a full-energy peak which is generated by self-decay of a scintillator containing a radioactive isotope in a PET detector system, in a drifted energy spectrum diagram after a gain value of the PET detector system has changed, i.e., a current total peak position of a module; the second acquisition module is configured to acquire a ratio of a currently accumulated energy of each signal channel to a total currently accumulated energy of all signal channels in the PET detector system, i.e., a proportion of a current energy of each signal channel to a total energy, after the gain value of the PET detector system has changed; the calculation module is configured to substitute the current total peak position of the module, the proportion of the current energy of each signal channel to the total energy and a target total peak position of the module, and a proportion of a target energy of each signal channel to the total energy into the following formula to calculate a gain adjustment ratio of each signal channel:

$$A(x) = \frac{Pref * Gref(x)}{Pcur * Gcur(x)},$$

wherein, x represents a signal channel number which is an integer from 1 to N, and N is a total signal channel number in the PET detector system; A(x) is a gain adjustment ratio of a signal channel x; Pref is a target total peak position of the module; Gref(x) is a proportion of the target energy of the signal channel x to the total energy; Pcur is a current total peak position of the module; Gcur(x) is a proportion of the current energy of the signal channel x to the total energy; the target total peak position of the module is an initial channel number of a peak position of a full-energy peak which is generated by self-decay of the scintillator containing the radioactive isotope in the PET detector system, in an initial energy spectrum diagram; the proportion of the target energy of each signal channel to the total energy is a ratio of an initially accumulated energy of each signal channel to a total initially accumulated energy of all of the signal channels in the PET detector system; and
the adjustment module is configured to, perform gain adjustment for each signal channel respectively according to the gain adjustment ratio of each signal channel.

14. The correction system according to claim 13, wherein the first acquisition module is specifically configured to:
accumulate energies of all of the self-decay cases to form an energy spectrum after a gain value of the PET detector system has changed; acquire, according to the energy spectrum, a drifted channel number of a peak position of a full-energy peak which is generated by self-decay of a scintillator containing a radioactive isotope in the PET detector system, in the drifted energy spectrum diagram after the gain value of the PET detector system has changed.

15. The correction system according to claim 13, wherein the first acquisition module is specifically configured to:
accumulate energies of the self-decay cases in a preset region to form an energy spectrum after the gain value of the PET detector system has changed; acquire, according to the energy spectrum, drifted channel numbers of peak positions of a plurality of full-energy peaks which is generated by self-decay of a scintillator containing a radioactive isotope in the PET detector system, in a drifted energy spectrum diagram after the gain value of the PET detector system has changed; and calculate a sum or an average of the drifted channel numbers of the peak positions of the plurality of full-energy peaks to obtain the current total peak position of the module.

16. The correction system according to claim 13, wherein the second acquisition module comprises:
a collection unit configured to collect a plurality of self-decay cases of the scintillator containing the radioactive isotope in the PET detector system after the gain value of the PET detector system has changed;
a first calculation unit configured to calculate the currently accumulated energy of each signal channel in the plurality of self-decay cases of the scintillator containing the radioactive isotope;
a second calculation unit configured to calculate the total currently accumulated energy of all of the signal channels in the plurality of self-decay cases of the scintillator containing the radioactive isotope; and
a third calculation unit configured to calculate the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

17. The correction system according to claim 16, wherein, the collection unit is configured to collect a plurality of self-decay cases of the scintillator containing the radioactive isotope in the PET detector system after the gain value of the PET detector system has changed;
the first calculation unit is configured to calculate the currently accumulated energy of each signal channel which passes through a present energy window in a preset region in the plurality of self-decay cases of the scintillator containing the radioactive isotope;
the second calculation unit is configured to calculate the total currently accumulated energy of all of the signal channels which pass through the present energy window in the region in the plurality of self-decay cases of the scintillator containing the radioactive isotope;
the third calculation unit is configured to calculate the ratio of the currently accumulated energy of each signal channel to the total currently accumulated energy of all signal channels, i.e., the proportion of the current energy of each signal channel to the total energy, in the plurality of self-decay cases of the scintillator containing the radioactive isotope.

18. The correction system according to claim 13, wherein the correction system further comprises:
a third acquisition module configured to acquire the initial channel number of the peak position of the full-energy peak which is generated by self-decay of the scintillator containing the radioactive isotope in the PET detector system, in the initial energy spectrum diagram of the PET detector system, i.e., the target total peak position of the module; and
a fourth acquisition module configured to acquire the ratio of the initially accumulated energy of each signal channel to the total initially accumulated energy of all of the signal channels in the PET detector system, i.e., the proportion of the target energy of each signal channel to the total energy.

19. The correction system according to claim 18, wherein, the third acquisition module is configured to acquire the initial channel number of the peak position of the full-energy peak which is generated by self-decay of the scintillator containing the radioactive isotope in the PET detector system, in the initial energy spectrum diagram, i.e., the target total peak position of the module;
the fourth acquisition module is configured to acquire the ratio of the initially accumulated energy of each signal channel to the total accumulated energy of all of the initial signal channels in the PET detector, i.e., the proportion of the target energy of the signal channel x to the total energy;
the first acquisition module is configured to acquire the drifted channel number of the peak position of the full-energy peak which is generated by self-decay of the scintillator containing the radioactive isotope in the PET detector system, in the drifted energy spectrum diagram, i.e., the current total peak position of the module;
the second acquisition module is configured to: calculate and output, after acquiring, by the PET detector system, a plurality of self-decay cases of the scintillator acquired randomly, the accumulated energy of each signal channel in the plurality of self-decay cases of the scintillator; and calculate the current ratio of the accumulated energy of each signal channel to the total accumulated energy of all signal channels, i.e., the proportion of the current energy of the signal channel x to the total energy, in the plurality of self-decay cases of the scintillator respectively;
the calculation module is configured to calculate a gain adjustment ratio of each signal channel respectively according to the following formula:

$$A(x) = \frac{Pref * Gref(x)}{Pcur * Gcur(x)},$$

in which, x represents a signal channel number which is an integer from 1 to N, and N is a total signal channel number in the PET detector system and is an integer larger than or equal to 4;
A(x) is the gain adjustment ratio of the signal channel x;
Pref is the target total peak position of the module;
Gref(x) is the proportion of the target energy of the signal channel x to the total energy;
Pcur is the current total peak position of the module;
Gcur(x) is the proportion of the current energy of the signal channel x to the total energy; and the adjustment module configured to, perform gain adjustment for each signal channel respectively according to the gain adjustment ratio of each signal channel.

20. The correction system according to claim 19, wherein, the third acquisition module is configured to acquire an initial channel number of a 307 key initial peak position which is generated by 176Lu self-decay of an LYSO crystal in the PET detector system, in the initial energy spectrum diagram, i.e., the target total peak position of the module;

the fourth acquisition module is configured to acquire the ratio of the initially accumulated energy of each signal channel to the total accumulated energy of all of the initial signal channels, i.e., the proportion of the target energy of the signal channel x to the total energy in the PET detector;

the first acquisition module is configured to acquire a drifted channel number of a 307 key initial peak position which is generated by 176Lu self-decay of the LYSO crystal in the PET detector system, in the drifted energy spectrum diagram, i.e., the current total peak position of the module;

the second acquisition module is configured to: calculate and output, after acquiring, by the PET detector system, a plurality of LYSO self-decay cases acquired randomly, the accumulated energy of each signal channel in the plurality of LYSO self-decay cases; and calculate the current ratio of the accumulated energy of each signal channel to the total accumulated energy of all signal channels, i.e., the proportion of the current energy of the signal channel x to the total energy, in the plurality of LYSO self-decay cases respectively;

the calculation module is configured to calculate the gain adjustment ratio of each signal channel respectively according to the following formula:

$$A(x) = \frac{Pref * Gref(x)}{Pcur * Gcur(x)},$$

in which, x is an integer larger than or equal to 4;
A(x) is the gain adjustment ratio of the signal channel x;
Pref is the target total peak position of the module;
Gref(x) is the proportion of the target energy of the signal channel x to the total energy;
Pcur is the current total peak position of the module;
Gcur(x) is the proportion of the current energy of the signal channel x to the total energy; and
the adjustment module configured to, perform gain adjustment for each signal channel respectively according to the gain adjustment ratio of each signal channel.

\* \* \* \* \*